US009504436B2

(12) United States Patent
Suri et al.

(10) Patent No.: US 9,504,436 B2
(45) Date of Patent: *Nov. 29, 2016

(54) METHOD FOR BREAST SCREENING IN FUSED MAMMOGRAPHY

(71) Applicant: Hologic, Inc., Bedford, MA (US)

(72) Inventors: Jasjot S Suri, Westminister, CO (US); Yajie Sun, Westminister, CO (US); Roman Janer, Englewood, CO (US)

(73) Assignee: Hologic, Inc., Bedford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/694,836

(22) Filed: Nov. 30, 2012

(65) Prior Publication Data

US 2013/0251103 A1 Sep. 26, 2013

Related U.S. Application Data

(63) Continuation of application No. 11/632,078, filed as application No. PCT/US2005/023998 on Jul. 7, 2005, now Pat. No. 8,326,006.

(60) Provisional application No. 60/586,850, filed on Jul. 9, 2004.

(51) Int. Cl.
A61B 6/00 (2006.01)
A61B 8/08 (2006.01)
G06T 7/00 (2006.01)

(52) U.S. Cl.
CPC .............. *A61B 6/52* (2013.01); *A61B 6/4417* (2013.01); *A61B 6/502* (2013.01); *A61B 6/5247* (2013.01);
(Continued)

(58) Field of Classification Search
CPC ...... A61B 6/52; A61B 6/502; A61B 6/5247; A61B 6/0825; A61B 6/5238; A61B 6/4417; G01T 7/0012; G01T 7/0083; G01T 7/0091; G01T 7/0095; G01T 2207/10112; G01T 2207/10116; G01T 2207/10136

USPC .......................................... 378/128, 130–132
See application file for complete search history.

(56) References Cited

U.S. PATENT DOCUMENTS 5,627,907 A 5/1997 Gur et al.
5,784,482 A 7/1998 Nakajima
(Continued)

FOREIGN PATENT DOCUMENTS

DE 10305640 2/2002
JP 02079177 9/1988
(Continued)

OTHER PUBLICATIONS

International Preliminary Report on Patentability in connection with PCT/US2005/023998.
(Continued)

Primary Examiner — Irakli Kiknadze
(74) Attorney, Agent, or Firm — Cooper & Dunham LLP

(57) ABSTRACT

A method for use in medical imaging of a patient including, with the patient immobilized with respect to an imaging reference frame, acquiring first digital imaging information including a first region of interest using a first imaging modality; processing the first digital imaging information to identify a feature for analysis; and using a second imaging modality to acquire targeted second imaging information for a second region of interest, the second region of interest corresponding to a subset of the first region of interest, wherein the second region of interest includes the feature for analysis. An apparatus for use in medical imaging comprising structure for immobilizing a patient with respect to an imaging reference frame; a first imaging system for acquiring first digital imaging information including a first region of interest using a first imaging modality; a processor processing the first digital imaging information using a diagnostic tool to identify a feature of interest; and a second imaging system for acquiring second imaging information using a second imaging modality, the second imaging information corresponding to a second region of interest including the feature for analysis.

20 Claims, 30 Drawing Sheets

(52) U.S. Cl.
CPC ........... *A61B 8/0825* (2013.01); *A61B 8/5238* (2013.01); *G06T 7/0012* (2013.01); *G06T 7/0083* (2013.01); *G06T 7/0091* (2013.01); *G06T 7/0095* (2013.01); *G06T 2207/10112* (2013.01); *G06T 2207/10116* (2013.01); *G06T 2207/10136* (2013.01); *G06T 2207/20016* (2013.01); *G06T 2207/20076* (2013.01); *G06T 2207/20168* (2013.01); *G06T 2207/30068* (2013.01); *G06T 2207/30096* (2013.01)

(56) References Cited

U.S. PATENT DOCUMENTS

| | | | |
|---|---|---|---|
| 5,832,103 | A | 11/1998 | Giger et al. |
| 5,999,639 | A | 12/1999 | Rogers et al. |
| 6,058,322 | A | 5/2000 | Nishikawa et al. |
| 6,115,488 | A | 9/2000 | Rogers et al. |
| 6,205,347 | B1 | 3/2001 | Morgan et al. |
| 6,282,305 | B1 | 8/2001 | Huo et al. |
| 6,396,940 | B1 | 5/2002 | Carrott et al. |
| 6,574,304 | B1 | 6/2003 | Hsieh et al. |
| 6,650,766 | B1 | 11/2003 | Rogers et al. |
| 6,687,329 | B1 | 2/2004 | Hsieh et al. |
| 6,928,142 | B2 * | 8/2005 | Shao et al. ............... 378/63 |
| 8,326,006 | B2 * | 12/2012 | Suri et al. ............... 382/128 |
| 2003/0149364 | A1 | 8/2003 | Kapur |
| 2003/0194050 | A1 | 10/2003 | Eberhard et al. |
| 2003/0208116 | A1 | 11/2003 | Liang et al. |

FOREIGN PATENT DOCUMENTS

| | | |
|---|---|---|
| JP | 09024035 | 7/1995 |
| JP | 11099077 | 6/1997 |
| JP | 2004089212 | 8/2002 |
| WO | 200617101 | 2/2006 |

OTHER PUBLICATIONS

Kapur A et al: "Fusion of Digital Mammography With Breast Ultrasound—A Phantom Study" Proceedings of the SPIE, SPIE, US LNKD-DOI:10.1117/12.465597, vol. 4682, Feb. 24, 2002 (Feb. 24, 2002), pp. 526-537, XP008044412 ISSN: 0277-786X http://dx.doi.org/10.1117/12.465597.

Cheng H D et al: "Computer-aided detection and classification of microcalcifications in mammograms: a survey" Pattern Recognition, Elsevier, GB LNKD-DOI:10.1016/S0031-3203(03)00192-4, vol. 36, No. 12, Dec. 1, 2003) Dec. 1, 2003, pp. 2967-2991, XP004461101 ISSN: 0031-3203 http://dx.doi.org/10.1016/S0031-3203(03)00192-4.

* cited by examiner

Radial Line Intersection Illustration

Multiresolution Downsampling

Classification System

METHOD FOR BREAST SCREENING IN FUSED MAMMOGRAPHY

CROSS-REFERENCE TO RELATED APPLICATIONS

This application is a continuation of, U.S. patent application Ser. No. 11/632,078, filed Oct. 20, 2008 which is a national stage of PCT International Application No. PCT/US2005/23998, filed Jul. 7, 2005, which claims the benefit of U.S. Provisional Application No. 60/586,850, filed Jul. 9, 2004, entire contents of each of which are hereby incorporated by reference in their entireties.

FIELD

Embodiments of the present invention relate generally to breast screening in fused mammography, and more specifically to analyzing a feature of interest by imaging a first region of interest using a first modality and imaging a second region of interest using a second modality, wherein the first and second regions of interest include the feature of interest.

BACKGROUND

In the field of medical imaging, various modalities are available, such as magnetic resonance imaging (MRI) and computed tomography (CT). Fusion (i.e., combined use) of multiple imaging modalities has been employed for the past decade and is still in its infancy stage. Fusion of MR and CT was first, due in part to the digital nature of these modalities. Because conventional approaches toward fusion of MR and CT typically use the entire breast volume for processing, the associated combined algorithms are computationally intensive. As such, conventional fusion approaches are often not practical in image-guided surgery and real-time breast imaging applications.

FIG. 1 and FIG. 2 show one example of a conventional approach of combined medical imaging modalities as disclosed by General Electric Company. The system generates 3-D X-ray volumetric slices using the 3-D tomosynthesis principle (Wu et al.). A second stage involves 3-D ultrasound (US) scanning using a US transducer, which is used to scan on the top of a plastic sheet. The output includes multiple 3-D ultrasound slices.

SUMMARY

An embodiment of a method for use in medical imaging of a patient includes, with the patient immobilized with respect to an imaging reference frame, acquiring first digital imaging information including a first region of interest using a first imaging modality; processing the first digital imaging information to identify a feature for analysis; and using a second imaging modality to acquire targeted second imaging information for a second region of interest, the second region of interest corresponding to a subset of the first region of interest, wherein the second region of interest includes the feature for analysis.

An embodiment of an apparatus for use in medical imaging includes structure for immobilizing a patient with respect to an imaging reference frame; a first imaging system for acquiring first digital imaging information including a first region of interest using a first imaging modality; a processor processing the first digital imaging information using a diagnostic tool to identify a feature of interest; and a second imaging system for acquiring second imaging information using a second imaging modality, the second imaging information corresponding to a second region of interest including the feature for analysis.

DETAILED DESCRIPTION

Figure 1:
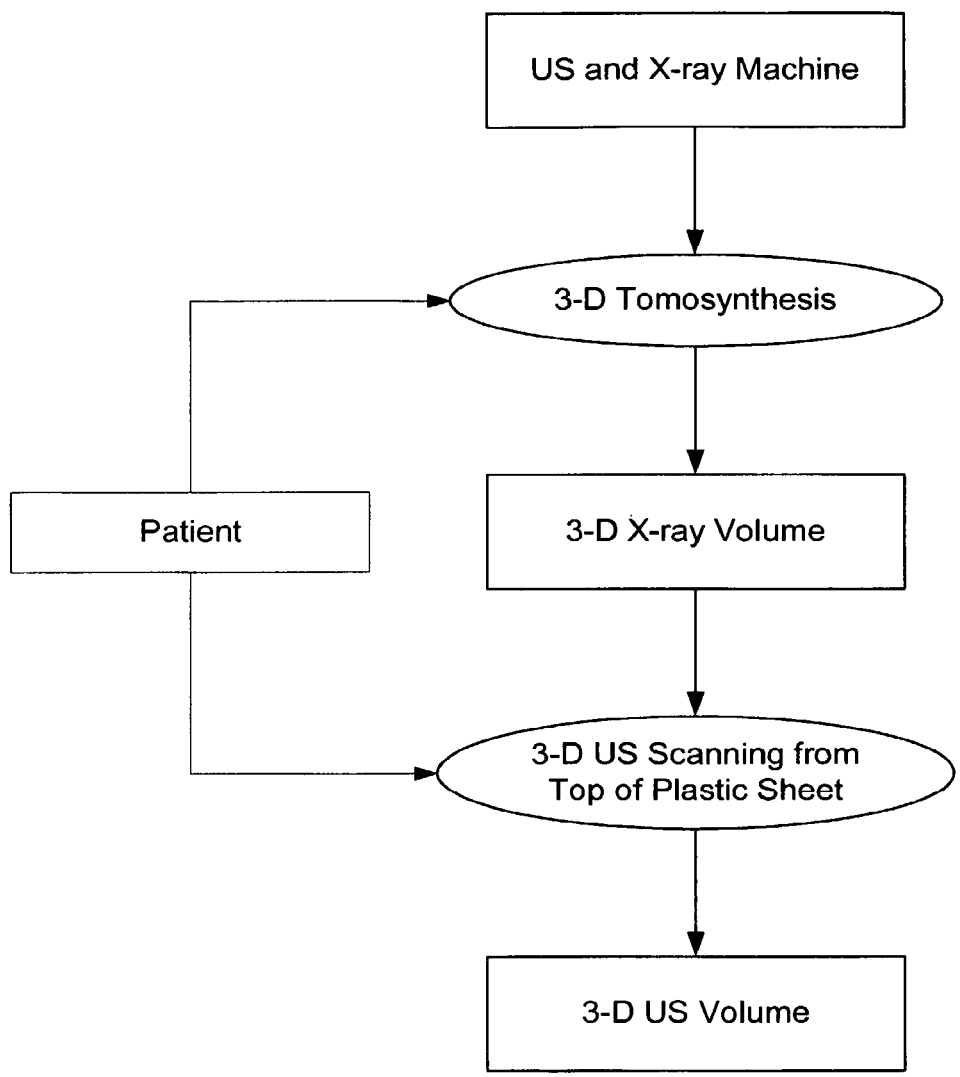
FIG. 1 and FIG. 2 show one example of a conventional approach of combined medical imaging modalities as disclosed by General Electric Company.
Figure 2:
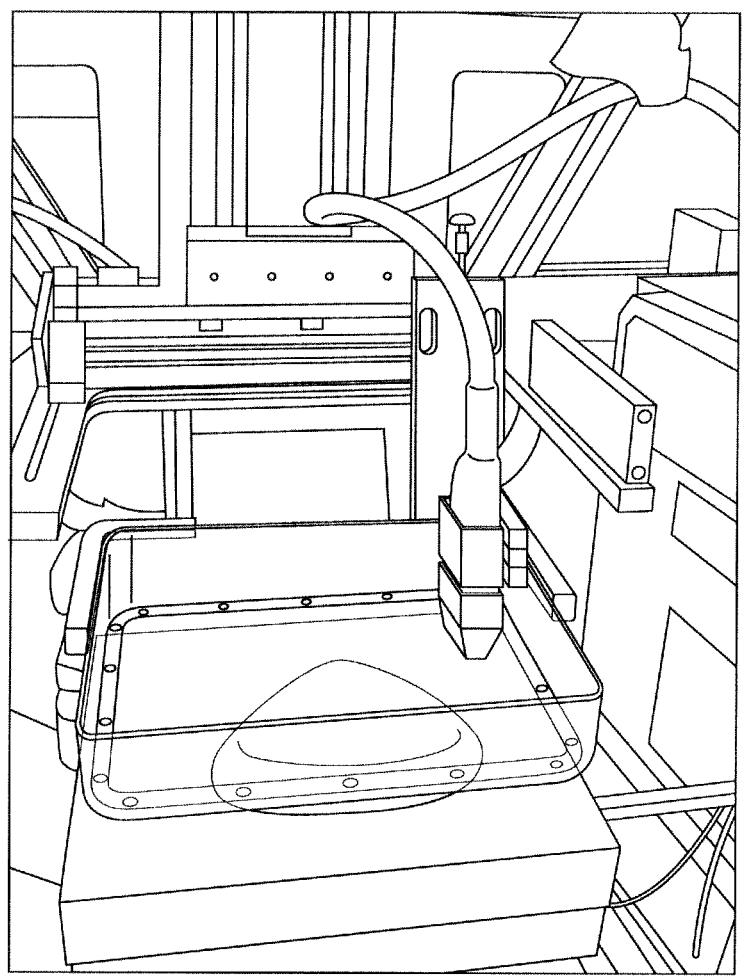

In the conventional computer-aided detection (CAD) systems, tumor detection is done after an image is acquired. Time is seldom a critical issue in the development of the CAD systems. However, in some implementations of full field digital mammography (FFDM) with ultrasound (US), time can be critical. In such implementations a fast CAD method is needed to guide the following ultrasound imaging system to acquire images of the tumor area only. Hence, the method reduces the time of ultrasound imaging.

Various embodiments of systems described herein include an off-line development and training system, and a fast on-line classification system. The system is developed and trained offline; e.g., outside of the time-frame of a medical imaging procedure. The training parameters resulting from the training system are then used online to transform the input test images that help in fast lesion detection system.

In a particular embodiment, a lesion detection system includes two stages. In stage one, initial segmentation is performed in a region of interest (ROI). Stage two includes elimination of false positives using training coefficients that are generated from a knowledge database developed in the offline training system. Before initial segmentation, the breast area of a screening mammogram is segmented from the background using a combination of spline fitting and thresholding to preserve the breast-skin boundary. The breast mask is expanded along the boundary to reduce the edge effects. This is defined as the Region of the Interest (ROI). The ROI image is then down sampled by a down-sampling factor (e.g., by four times) to reduce the image memory requirements and search space (e.g., by 16 times).

In some embodiments, initial segmentation involves thresholding followed by a morphological post-processing. Local adaptive thresholding based on a local histogram is used to improve the segmentation of low-contrast tumors. Initial segmentation is typically performed in the extracted breast areas.

In other embodiments, the segmented mass candidates includes ground-truth tumors and false positives. In stage two, a classification method is used to differentiate true positives from false positives. Features and/or measures are extracted from the lesion candidates in order to reduce the occurrence of false positive results. These features can be used to characterize true positives. Since processing time may be critical, a set of features with fast extraction is typically used. Features such as texture and shape are used in some embodiments. Texture features, such as features extracted from the Gray Level Co-occurrence Matrix (GLCM) or the Gabor filters are used. Shapes features extracted from the boundary of the candidate are also important to classify ground-truth tumors from false positives. These features then can be used to build a classifier through supervised training on a known database. A decision tree classifier is used in some embodiments. The training of a classifier is done offline. The training parameters will then be used online for lesion detection.

In accordance with various embodiments, the online lesion detection system uses the trained classifier parameters on the test mammographic images. This can be used to differentiate unknown mass candidates obtained from the initial segmentation step. Fast feature extraction typically will not take much time, but will eliminate a large number of false positives.

Three-dimensional (3-D) breast volumes can be fused with two-dimensional (2-D) projection images to facilitate breast imaging. Two different modalities can be used. For example, a handheld ultrasound can be used in conjunction with X-ray projection images. Embodiments described herein are directed toward fusion of X-ray projection images and 3-D ultrasound images. To facilitate the diagnostic ability of this process, an ultrasound projection image is computed from a 3-D ultrasound acquired using a customized ultrasound transducer (see, e.g., FIG. 5 below). The ultrasound projection image can be computed using a fan beam projection algorithm as used in 3-D computed tomography (CT) imaging. The X-ray projection image can be acquired using a scanning machine such as the SenoScan® machine from Fischer Imaging Corporation.

Various embodiments include a steering system that includes a software imaging method, which drives ultrasound image acquisition. The software imaging method renders the screening system fast and accurate. In addition, overall acquisition time is improved for scanning in fused modality framework.

Some embodiments provide for quick generation of diagnostic images of fused modalities. A potential benefit is the ability to provide a better picture of the lesions, their locations, and/or their growth factor (or angiogenesis of breast cancer).

In accordance with various embodiments, an isotropic volume can be generated. Isotropic volume generation can speed the scanning process because second modality scanning does not require scanning of the entire image.

System reliability of the system is ensured in various embodiments due to improved screening specificity and sensitivity. In addition, embodiments of processes incur less burden on diagnostic systems which use the fusion of the X-ray and ultrasound images.

Some embodiments of systems provide an integrated ultrasound scanner that enables accurate scanning. Inaccuracies associated with handheld US scanners can be avoided. In these embodiments, the US scanning is automatic in conjunction with the X-ray scanning system.

Various embodiments allow for extendibility of the system to a patient database. The system can be trained offline, and training parameter(s) are used for online lesion detection. Therefore, the training can be extended to a patient database offline in the development. The training parameters can be updated for online classification.

Embodiments provide for improved lesion detection by using segmentation to obtain initial lesion candidates. Features are used to reduce the likelihood of false positives. Through a supervised training on a large database, a large portion of false positives can be eliminated. Feature extraction reduces the number of false positives.

In accordance with some embodiments, segmentation of faint lesions is improved over conventional approaches. In these embodiments, localized adaptive thresholding improves the initial segmentation to obtain lesion candidates. Whereas segmentation based on the global thresholding may miss these lesions, localized thresholding can improve the segmentation of faint lesions. In addition, embodiments can include morphological processing, which allows for identification of solid and connected lesion candidates and removal of spurious dots.

Processing carried out by certain embodiments includes down-sampling to improve speed performance. Downsampling in a certain range will not degrade CAD performance for mass detection, but can greatly reduces the processing time. For example, if an image is downsampled four times in each direction, the speed can be up to sixteen times. In some embodiments, edge-preserving down-sampling is performed with multiresolution. Down-sampling typically involves anti-aliasing and low-pass filtering, which can have a blurring effect, which degrades the edges. Therefore, multiresolution based down-sampling can preserve sharpness of edges.

Various embodiments employ histogram-based thresholding in an automatic and adaptive manner. Because histogram-based thresholding gives automatic adaptive threshold selection, histogram-based thresholding generally improves thresholed results when compared to the results from the fixed threshold approaches.

In accordance with other embodiments breast mask extraction can improve speed and accuracy. Breast area segmentation from the background can reduce the processing area and improve the speed of processing. Breast mask extraction also reduces the inaccuracy that may occur if detection is used in the background.

In still other embodiments, spline fitting is employed to provide better breast-skin boundary extraction. Spline fitting in the narrow band allows for a continuous breast-skin boundary. The extracted boundary is closer to actual breast-skin line.

In yet other embodiments, shape and texture (e.g., from Gray-level Co-occurrence Matrices (GLCM) and/or Gabor transforms) features facilitate reduction of false positive results: Shape and texture features are used in CAD methods to differentiate true lesions from false positives. Boundary shape features can be a powerful tool in eliminating a large portion of false positives.

In some embodiments, multi-resolution (including wavelet) analysis is used to reduce the impact of effects due to breast and/or lesion size variation. Multi-resolution analysis can handle size variations, and is advantageous since breast area and lesion size varies with different patients.

In accordance with yet other embodiments, a list of features is maintained for purposes of system training. The collection of features in the training system allows the expansion of a database of lesion candidates. The collection of features is developed offline. A subset of features is used online. The expansion of the database may change the subset of features. New features can be developed and/or updated quickly. Online classification uses updated training parameters.

Various embodiments employs a decision tree, which serves as a fast, powerful classification tool. The decision tree can approach an arbitrary class boundary. In one embodiment, the decision tree can be trained or preset using a plurality of "if-then" rules.

In accordance with various embodiments, a fast lesion detection system includes a stand-alone computer-aided detection (CAD) system. Using the system, a physician has fast online lesion detection capability in real-time. High specificity of unequivocal negative mammogram of one view may prompt the physician to stop taking the other view. This can reduce the pain the patient endures and the X-ray exposure of the patient.

Some embodiments of the system are module-based. Modules can be implemented in software, hardware, firmware or any combination thereof. Software modules can allow for easy development and modification. In addition modules can be used for the stand-alone application, or be integrated into other systems.

Figure 3:
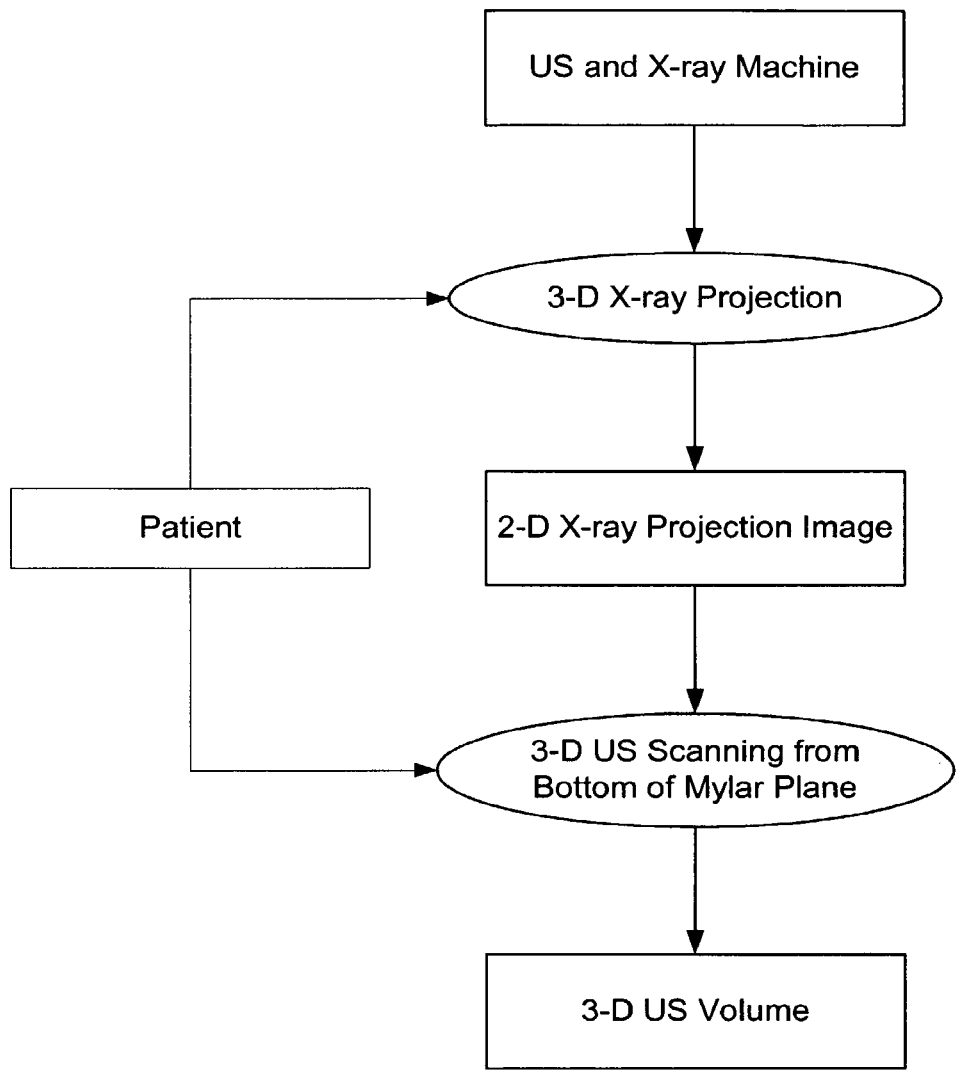
FIG. 3 illustrates one exemplary process for breast imaging with combined ultrasound (US) and X-ray imaging.
Figure 4:
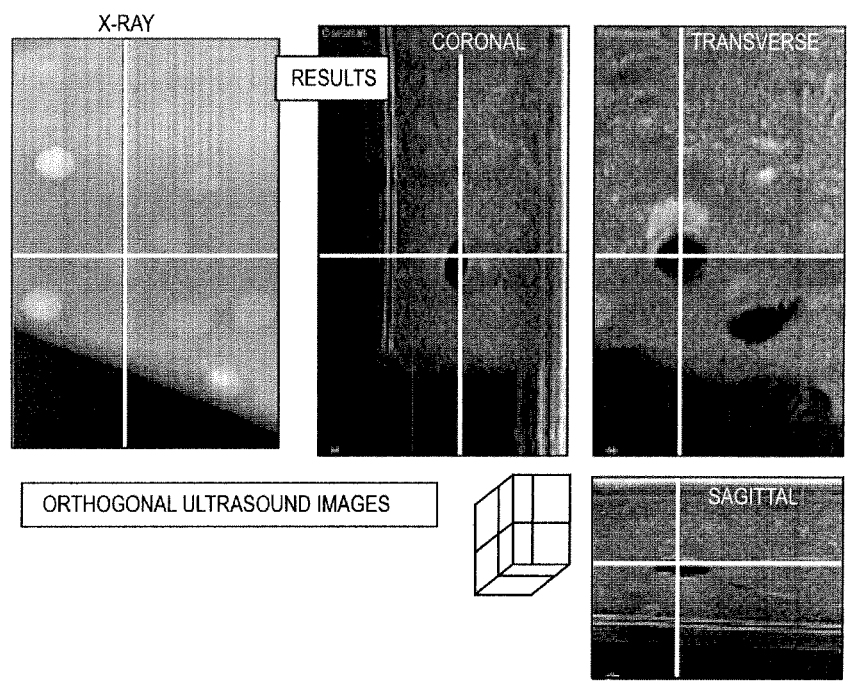
FIG. 4 illustrates exemplary images output from the US transducer stage.

FIG. 3 illustrates one exemplary process for breast imaging with combined ultrasound (US) and X-ray imaging. The process includes two stages. The first stage employs an X-ray scanning system, which uses 2-D X-ray projection images (as shown in the ellipse in FIG. 3). The second stage involves 3-D ultrasound scanning, wherein the ultrasound scanning is done using the ultrasound transducer by moving the transducer beneath the Mylar sheet. The output includes slices in three orthogonal directions: Sagittal, Coronal and Transverse. Exemplary images output from the US transducer stage are shown in FIG. 4.

Figure 5:
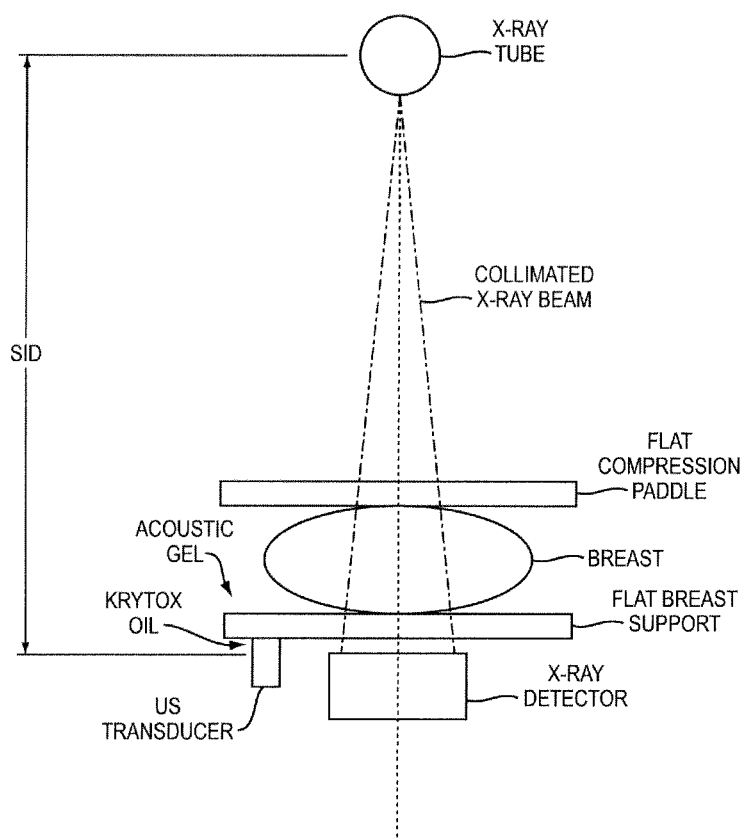
FIG. 5 illustrates an exemplary system in which image data acquisition can be performed in accordance with one embodiment.

FIG. 5 illustrates an exemplary system in which image data acquisition can be performed in accordance with one embodiment. This particular embodiment employs two modalities for screening. The breast to be scanned is positioned between the flat breast support and the breast paddle. The X-ray beams penetrate the patient's breast and the attenuation properties are captured at the digital detector. The image can be reconstructed using the digital detector principle. In the same system, the 3-D ultrasound breast slices are reconstructed. In accordance with one embodiment, breast slices are only scanned in the lesion area detected by a fast lesion detection system on the X-ray image.

Figure 6:
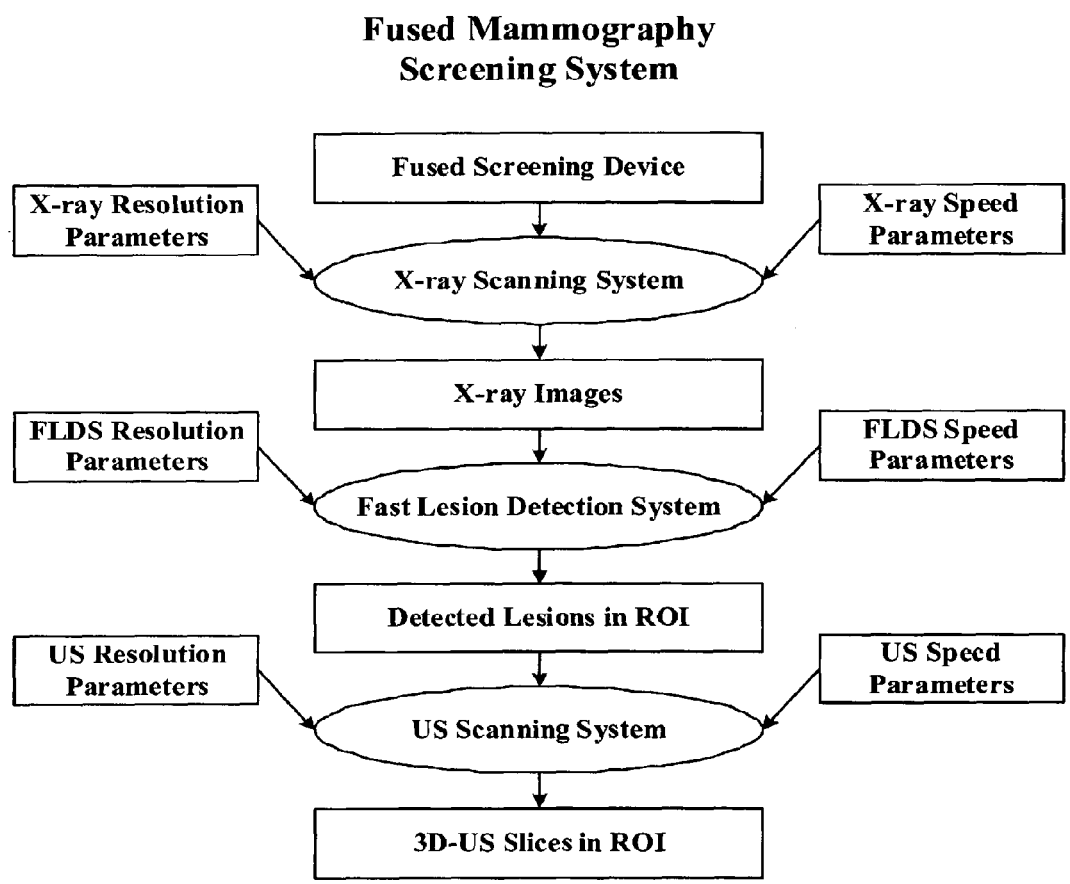
FIG. 6 illustrates an exemplary embodiment of a process carried out by a fused mammography screening system.

FIG. 6 illustrates an exemplary embodiment of a process carried out by a fused mammography screening system. As illustrated, two modalities are used for screening. The breast to be scanned is positioned between the flat breast support and the breast paddle. The X-ray beams penetrate the patient's breast and the attenuation properties are captured at the digital detector. The image is reconstructed using the digital detector principle. In the same system, we reconstruct the 3-D ultrasound breast slices. 3-D ultrasound breast slices are only scanned in the lesion area detected by our fast lesion detection system on the X-ray image.

Figure 7:
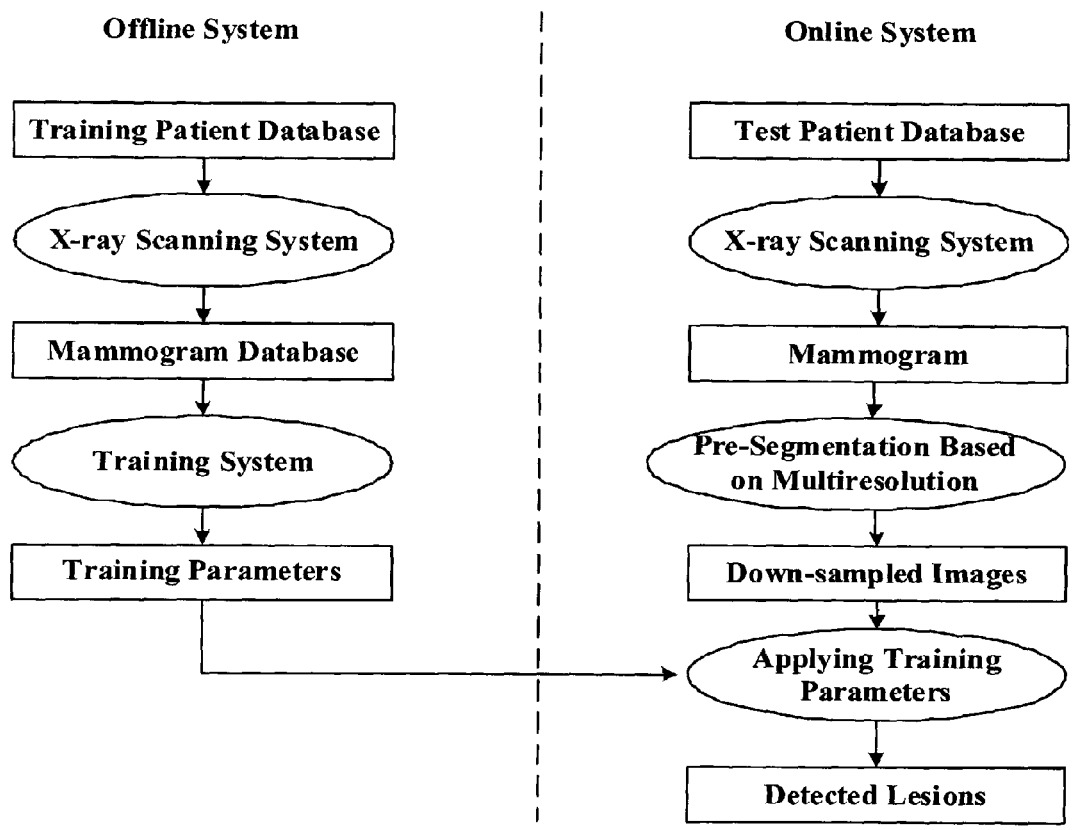
FIG. 7 illustrates an embodiment of a system for fast lesion detection.

FIG. 7 illustrates an embodiment of a system for fast lesion detection. The fast lesion detection system (FLDS) carries out processes in two phases: offline development and training and a fast online system. Phase one is offline system development and the training system. Phase two is real-time online fast lesion detection, which uses the training parameters from the phase one. Offline system involves X-ray image acquisition and the training system. Training parameters obtained from the training system are then used for online lesion detection. The online system includes three modules: an X-ray scanning system, a pre-segmentation based on multi-resolution, and a lesion detection system. Each module is discussed further below with regard to FIGS. 8-10.

Figure 8:
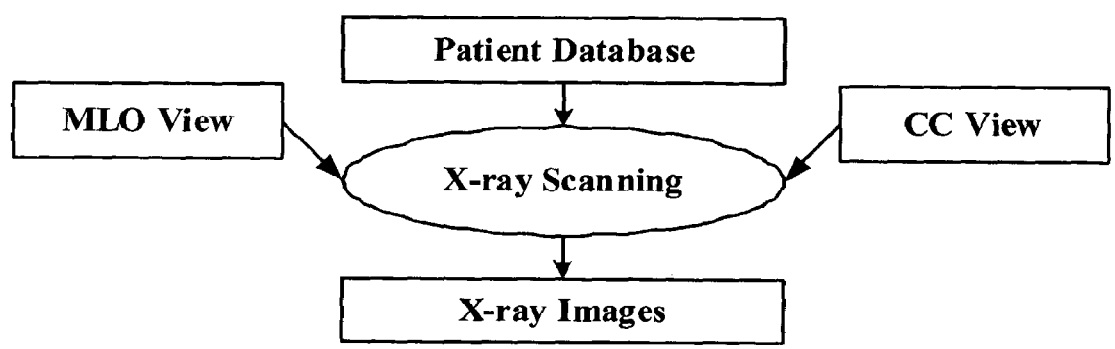
FIG. 8 shows an embodiment of the X-ray scanning system, which is used in both online and offline systems.

FIG. 8 shows an embodiment of the X-ray scanning system, which is used in both online and offline systems. Mammograms of two views are acquired from X-ray scanning machine. They are Medio-lateral Oblique (MLO) view and Cranio-caudal (CC) View.

Figure 9:
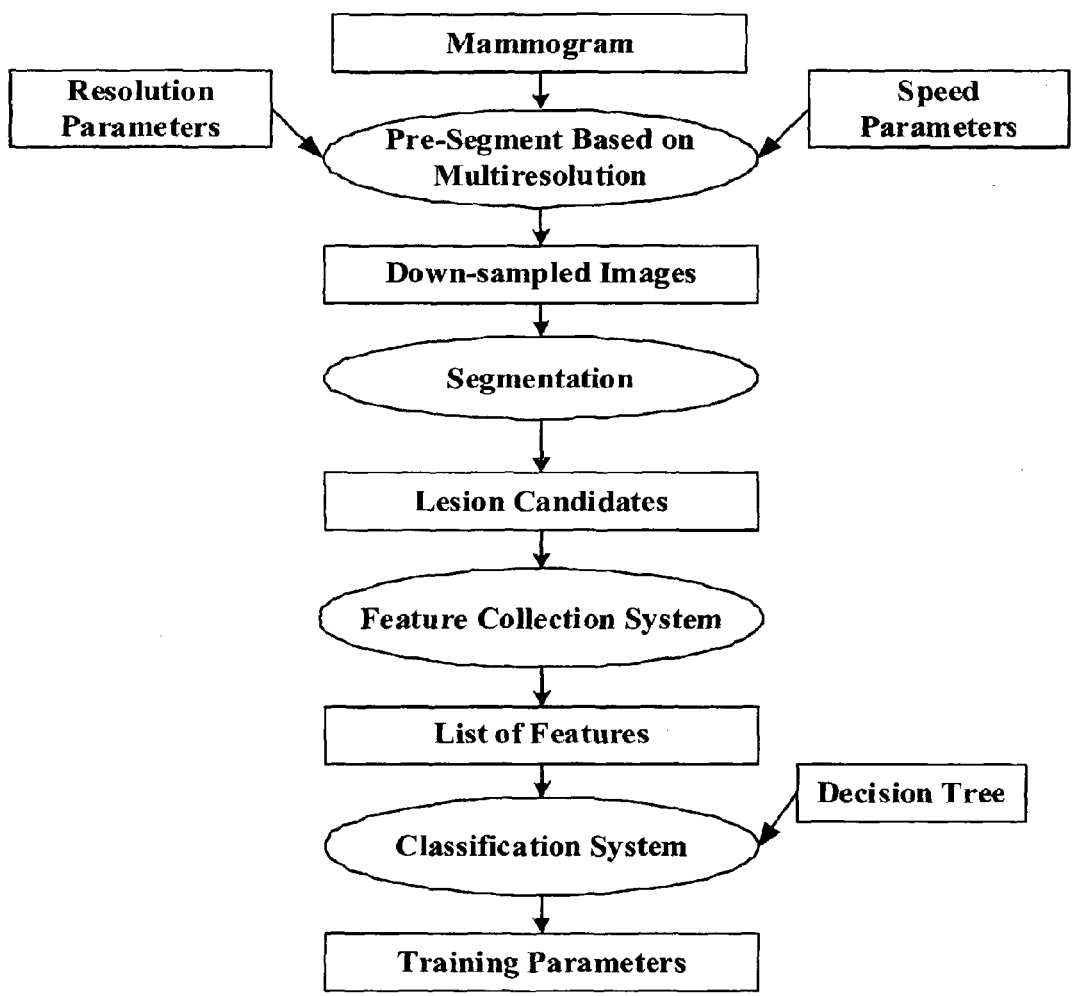
FIG. 9 shows exemplary procedures carried out by the training system shown in FIG. 7.

FIG. 9 shows exemplary procedures carried out by the training system shown in FIG. 7. Online lesion detection uses the training parameters obtained during the offline training. There are four stages in the training system. The first stage involves pre-segmentation based on multi-resolution analysis. In this stage, edge-preserving down-sampling is performed to reduce the processing time to meet the time constraint of FFDM/US system. In stage two, lesion candidates are obtained through segmentation. There can be a large number of false positives among lesion candidates. Stages three and four are used to eliminate most false positives through a supervised training processing. Stage three is a feature collection system, which defines a list of feature that could be used to separate false positives from true positives obtained from the segmentation step. A list of features is extracted to distinguish true positives from false positives. From the feature set, a classification system is built through training in the stage four. The training parameters from the classification stage will then be used for the online classification of unknown lesion candidates.

Figure 10:
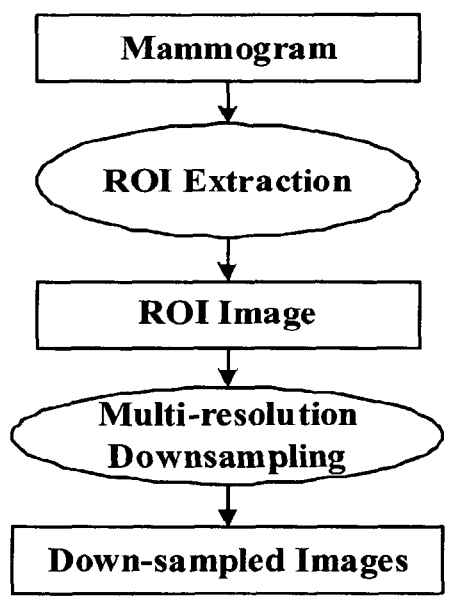
FIG. 10 illustrates an exemplary embodiment of a procedure for pre-segmentation based on multi-resolution.

An exemplary embodiment of a procedure for pre-segmentation based on multi-resolution is shown in FIG. 10. The procedure includes extraction of a Region of Interest (ROI) and multi-resolution downsampling. ROI extraction is used to obtain the breast area. The ROI is then down sampled by a factor to reduce the amount of data required to represent the image. In one particular embodiment, the ROI is down-sampled by four times in each direction to reduce the number of data bits in the image by 16 times. Down-sampling can increase the speed of processing.

Figure 11:
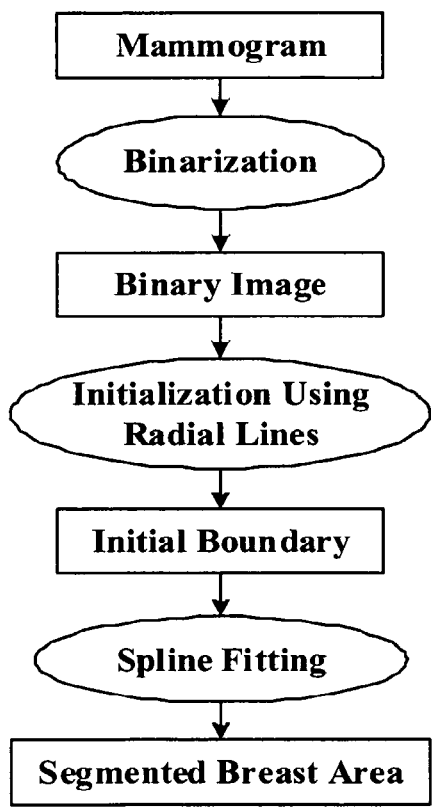
FIG. 11 illustrates an exemplary embodiment of the process of ROI extraction.
Figure 12:
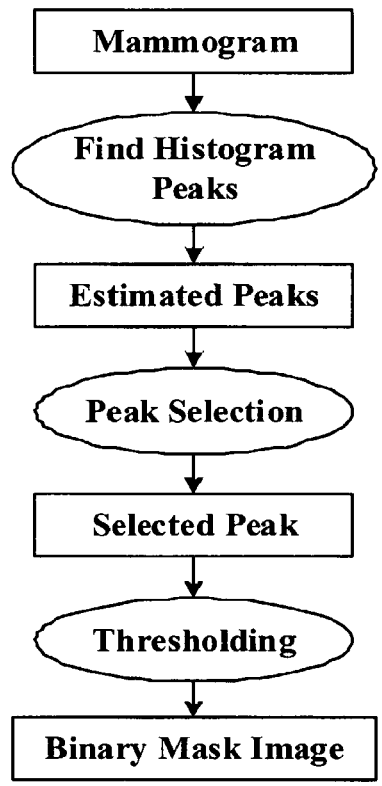
FIG. 12 illustrates an embodiment of the binarization step shown in FIG. 11.
Figure 13:
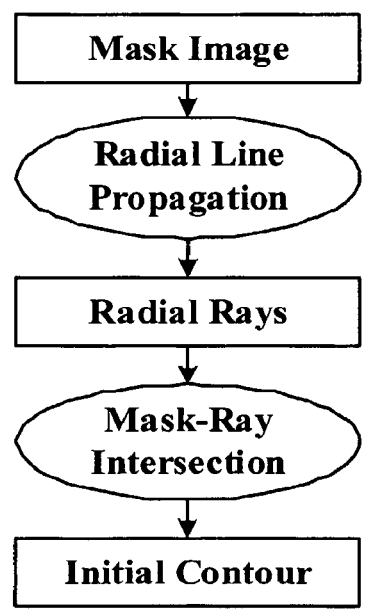
FIG. 13 illustrates an embodiment of the process of initialization with radial lines.
Figure 14:
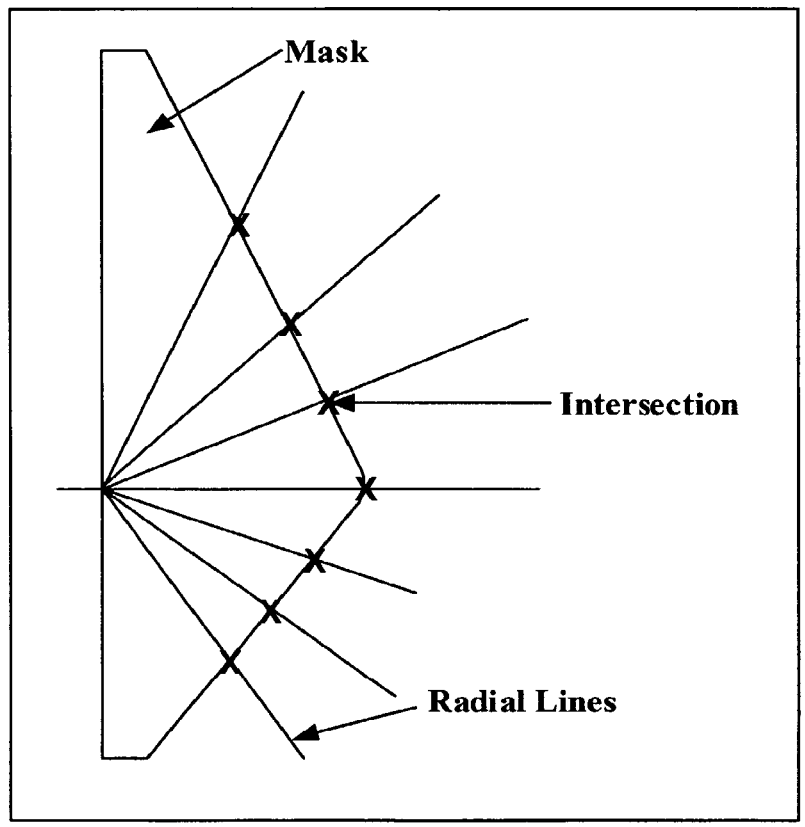
FIG. 14 illustrates exemplary radial line intersection.

FIG. 11 illustrates an exemplary embodiment of the process of ROI extraction. A mammogram is first binarized. A set of radial lines then draws from the chest wall toward skin boundary to obtain the initial boundary. Spline fitting is then used to obtain the segmented breast area and breast mask using the initial boundary as the starting contour. In FIGS. 12-14, three steps of ROI extraction process are described in further detail.

FIG. 12 illustrates an embodiment of the binarization step shown in FIG. 11. The binarization is based on the histogram analysis of breast area and background area. Peaks in the histogram are estimated, and then peaks corresponding to the breast area and the background area are selected. A threshold is automatically calculated between two peaks. A binary mask image is obtained after thresholding.

FIG. 13 illustrates an embodiment of the process of initialization with radial lines. FIG. 14 illustrates exemplary radial line intersection. Radial lines are drawn from the chest wall toward the skin boundary. From the intersection of radial lines and the binary mask image, an initial contour is obtained. Radial line intersection advantageously provides for fast extraction of the initial contour. The initial contour is then used to find the accurate breast-skin boundary.

Figure 15:
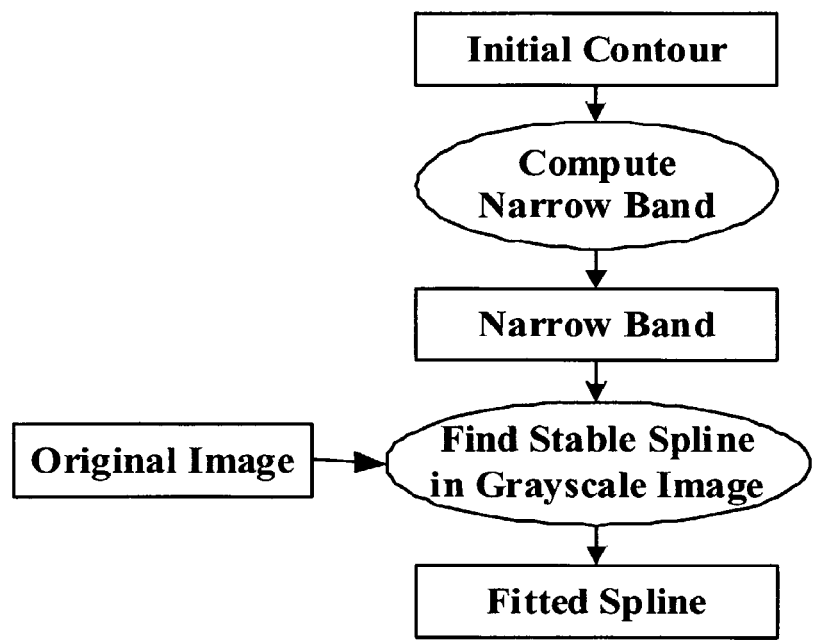
FIG. 15 illustrates an embodiment of the spline fitting process to obtain the accurate boundary of breast-skin segmentation.

FIG. 15 illustrates an embodiment of the spline fitting process to obtain the accurate boundary of breast-skin segmentation. From the initial contour, a narrow band is computed along the initial contour as the range for spline fitting. A stable spline found in the original image is the accurate and continuous boundary of the breast-skin. From the boundary, the segmented breast area can be obtained.

Figure 16:
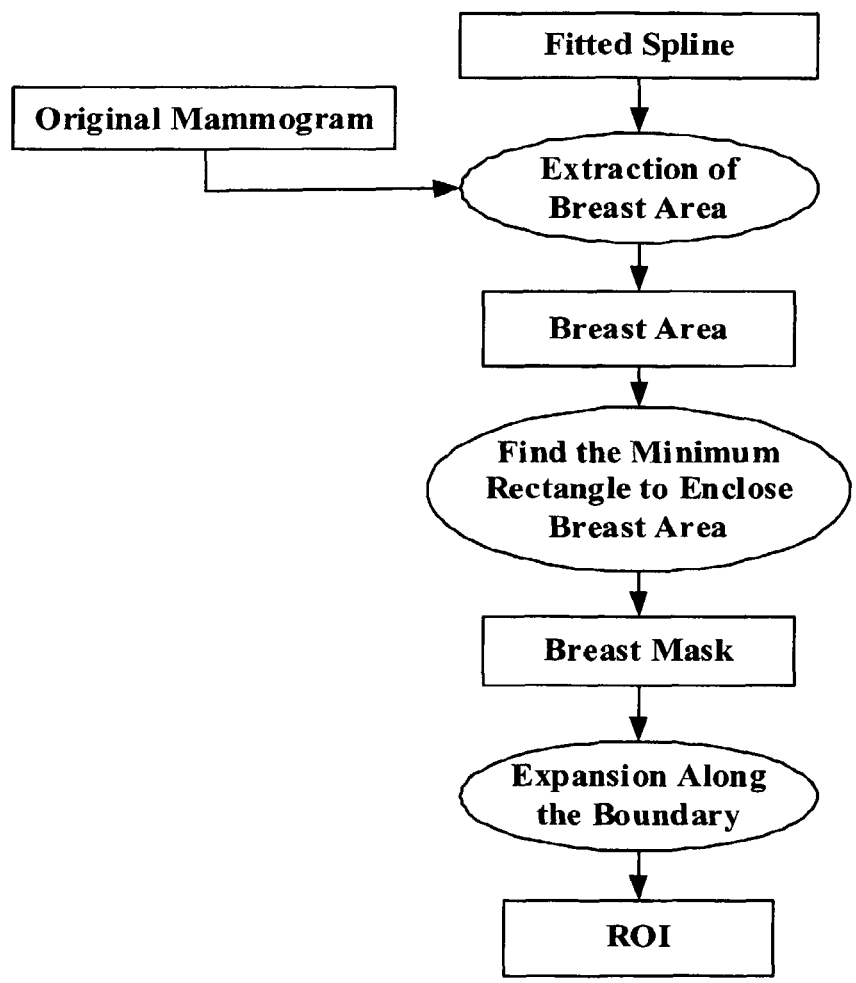
FIG. 16 depicts an embodiment of a process of extracting the Region of Interest (ROI)

FIG. 16 depicts an embodiment of a process of extracting the Region of Interest (ROI). In one embodiment, the processing steps are performed with respect to the extracted ROI. A minimum rectangle to enclose the segmented breast area is estimated. The estimated minimum rectangle is called a breast mask. The masked rectangular breast region is then expanded along the boundary to reduce the edge effects. This is called the Region of Interest (ROI).

Figure 17:
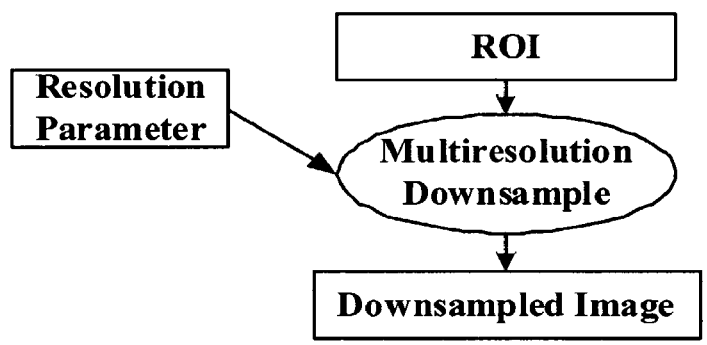
FIG. 17 is the block diagram illustrating an embodiment of a process of multi-resolution down-sampling.

FIG. 17 is the block diagram illustrating an embodiment of a process of multi-resolution down-sampling. Down-sampling involves anti-aliasing and low-pass filtering. Low-pass filtering can have a blurring effect, which causes the degradation of edges and sharp corners. Multi-resolution down-sampling advantageously preserves edges.

Figure 18:
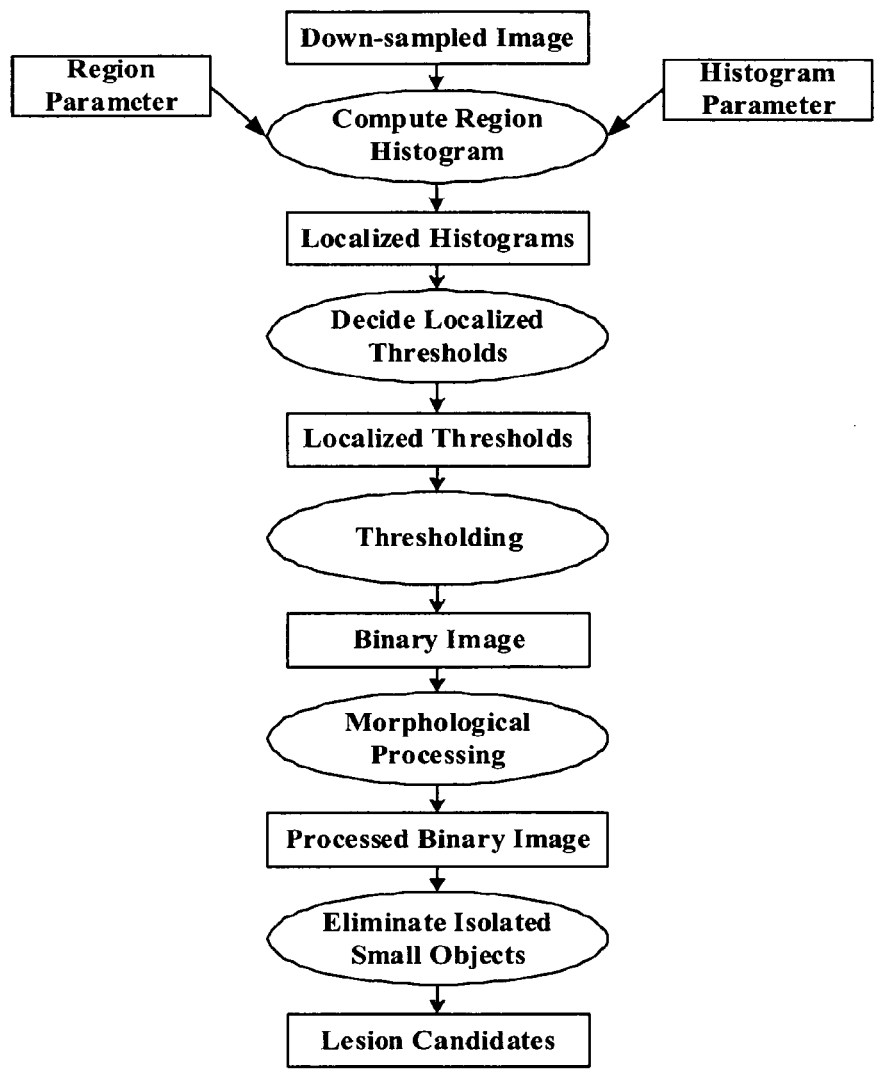
FIG. 18 is a block diagram illustrating one embodiment of a process of segmentation.

FIG. 18 is a block diagram illustrating one embodiment of a process of segmentation. The process includes adaptive local thresholding, morphological processing and removal of isolated small objects. The adaptive local thresholding based on the localized histogram improves the initial segmentation of breast lesions. Unlike the global thresholding, the adaptive thresholding can allow the detection of lesions of low-contrast. Morphological processing helps to merge neighboring segmented objects and remove the spurious isolated small objects. Morphological processing helps shape the segmented objects and reduce the number of lesion candidates. The final step of small isolated objects will further remove some very obvious false positives. These lesion candidates obtained will then be input to the detection system to reduce the false positives.

Figure 19:
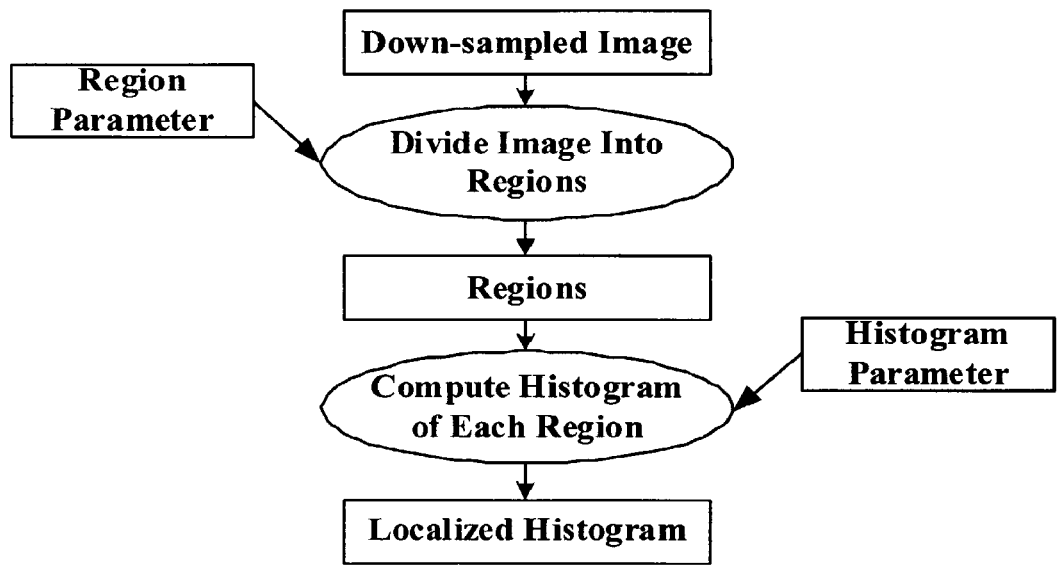
FIG. 19 illustrates an embodiment of a process for obtaining localized histograms from the down-sampled images.

FIG. 19 illustrates an embodiment of a process for obtaining localized histograms from the down-sampled images. The image is divided into regions. The region size is determined experimentally. A histogram is computed from each region.

Figure 20:
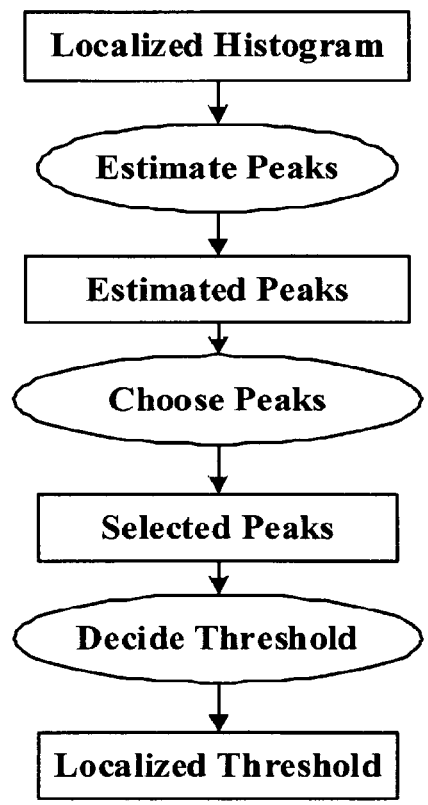
FIG. 20 is the block diagram illustrating an embodiment of a process for obtaining adaptive localized thresholds.

FIG. 20 is the block diagram illustrating an embodiment of a process for obtaining adaptive localized thresholds. Threshold is adaptive to each region. Therefore, a better segmentation can be obtained with thresholds adapted to the local regions.

Figure 21:
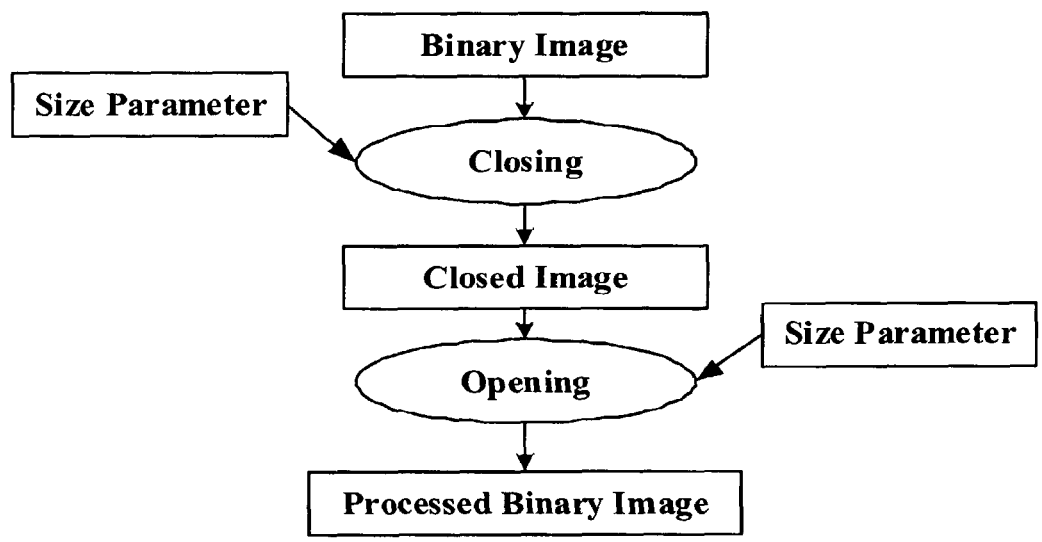
FIG. 21 is the block diagram illustrating an embodiment of morphological processing.

FIG. 21 is the block diagram illustrating an embodiment of morphological processing. Morphological closing is used to merge the neighboring binary objects. Due to gray level variation, some gray level objects in the image may be broken. Morphological closing can be used to obtain a continuous object. The morphological opening is used to remove spurious small isolated objects in the segmented image.

Figure 22:
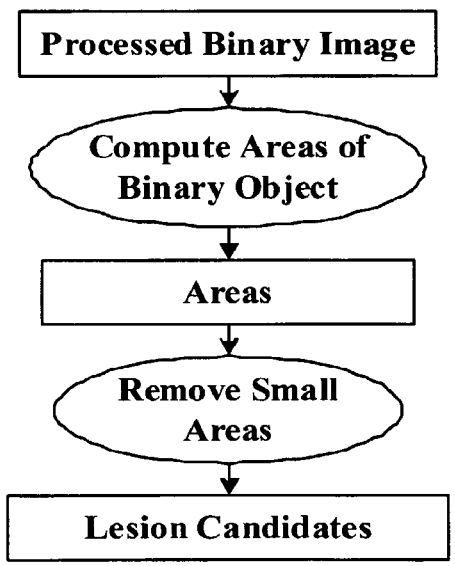
FIG. 22 is a block diagram illustrating an embodiment of a process for eliminating isolated small objects.

FIG. 22 is a block diagram illustrating an embodiment of a process for eliminating isolated small objects. This step is used to reduce very obvious false positives, which are small isolated objects. In one embodiment a simple technique is used to eliminate a large portion of false positives. If not removed, spurious objects may cause difficulties in the following lesion detection system.

Figure 23:
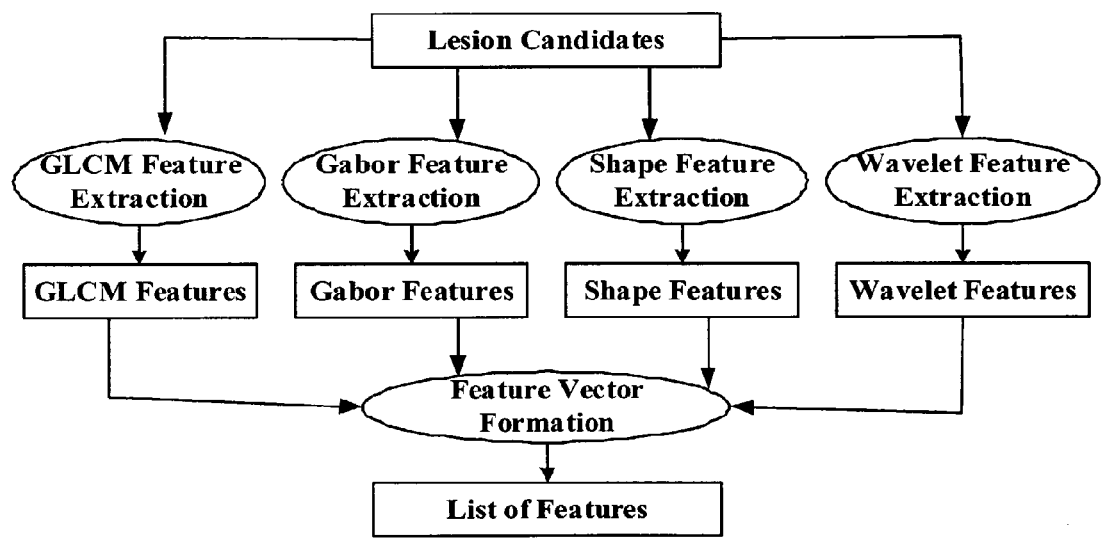
FIG. 23 is a block diagram illustrating an embodiment of a feature collection system.

FIG. 23 is a block diagram illustrating an embodiment of a feature collection system. The system performs four kinds of feature extraction. Texture feature extraction is performed using Gray Level Co-occurrence Matrix (GLCM) and Gabor filters. Shape features are also extracted to characterize the boundary of true positives from false positives. Wavelet features are used to account for the size variation of lesion candidates. Extracted features can be used later in the process for the training of a decision tree on a known database.

Figure 24:
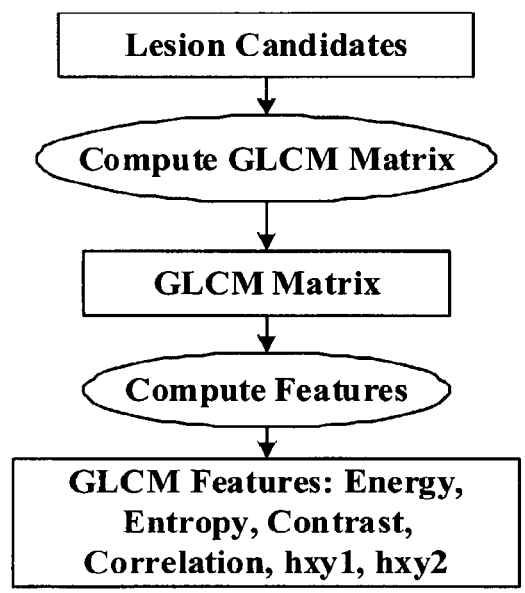
FIG. 24 is a block diagram illustrating an embodiment of GLCM feature extraction.

FIG. 24 is a block diagram illustrating an embodiment of GLCM feature extraction. The entry (i, j) of the GLCM matrix is computed as a relative frequency of a pair intensities (i, j) at a certain distance and a certain direction. From the GLCM, a set of features can be defined to characterize the texture information in the image. In one embodiment the feature defined in the original paper of GLCM by Haralick is used. By way of example, but not limitation, feature extraction can include Energy, Entropy, Contrast, and/or Correlation.

Figure 25:
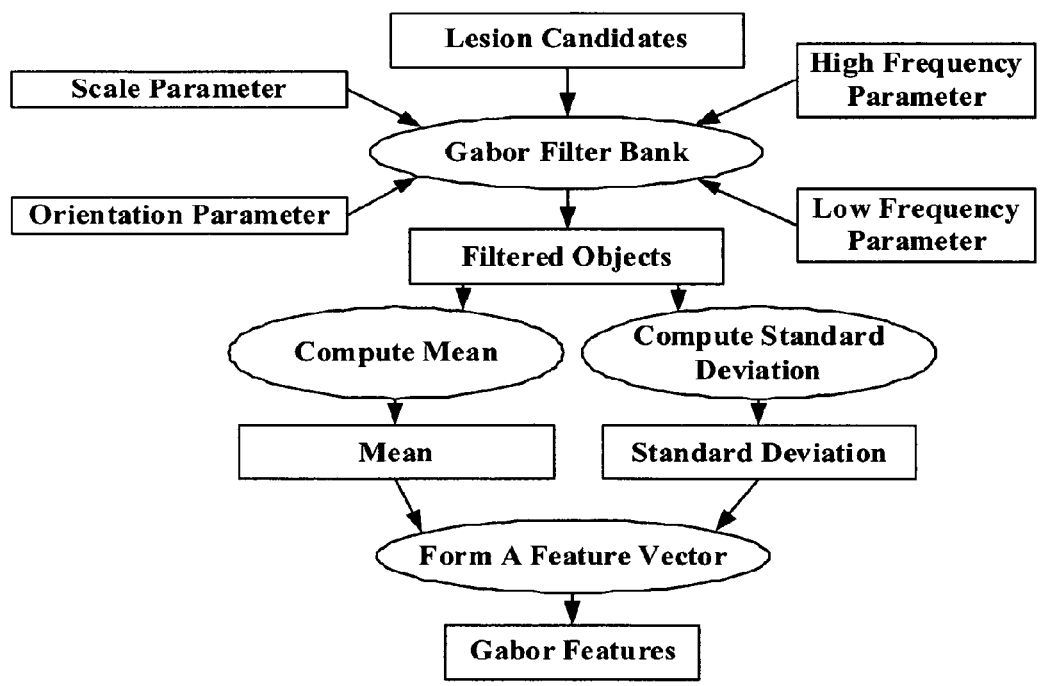
FIG. 25 is a block diagram illustrating an embodiment of Gabor feature extraction.

FIG. 25 is a block diagram illustrating an embodiment of Gabor feature extraction. From the mother Gabor, a Gabor filter bank can be obtained, which gives the spatial and frequency localization. From the Gabor filtered version of lesion candidates, the mean and standard deviation of the filtered candidates are computed as Gabor features. These features can be used for texture analysis and blob detection. The scale and orientation parameters determine the number of Gabor filters in the Gabor filter bank. The high and low frequency parameters are used to determine the frequency range of interest in analysis.

Figure 26:
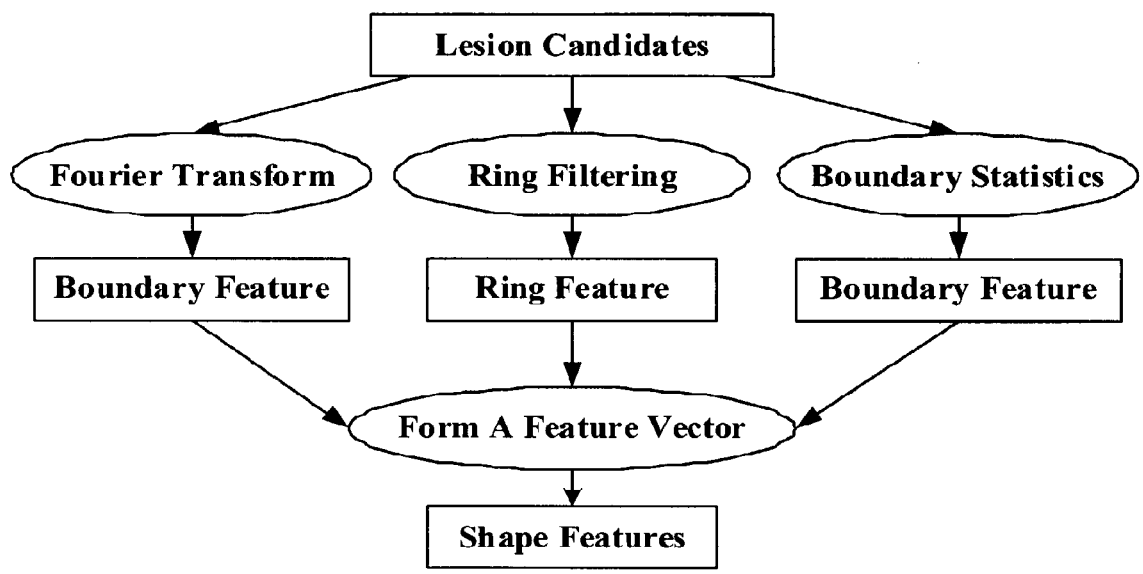
FIG. 26 is a block diagram illustrating a process of shape feature extraction.

FIG. 26 is a block diagram illustrating a process of shape feature extraction. Three types of processing are used to obtain shape features. First, Fourier descriptors are used to obtain shape features. Second, a ring filter is used to obtain the information of the boundary shapes. The final set of shape features is directly computed from the boundary to obtain the statistical features. These features can be used to differentiate the true positives from false positives since usually they have different characteristics.

Figure 27:
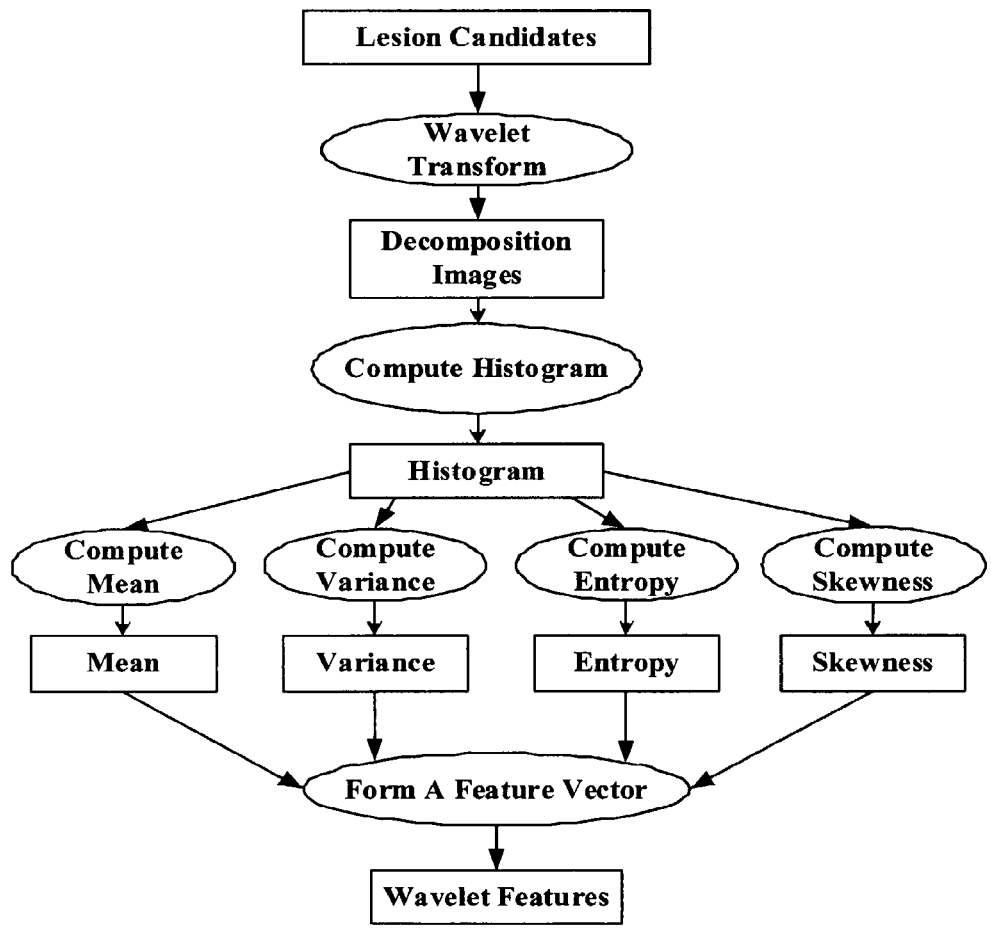
FIG. 27 is a block diagram illustrating one embodiment of a process of wavelet feature extraction.

FIG. 27 is a block diagram illustrating one embodiment of a process of wavelet feature extraction. Wavelet transformation can allow the multi-resolution analysis to capture the size variations of lesion candidates. In this embodiment, a set of statistical features, mean, variance, entropy and skewness, are computed from each decomposition image.

Figure 28:
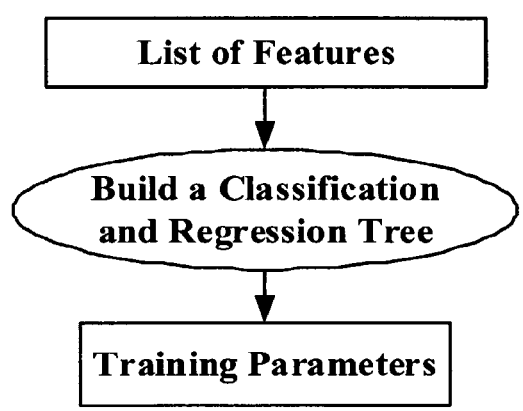
FIG. 28 is a block diagram of an exemplary embodiment of a classification system.

FIG. 28 is a block diagram of an exemplary embodiment of a classification system. From extracted features, a Classification and Regression Tree (CART) is built to obtain the training parameters. The training parameters will then be used online for fast detection of breast lesions.

Figure 29:
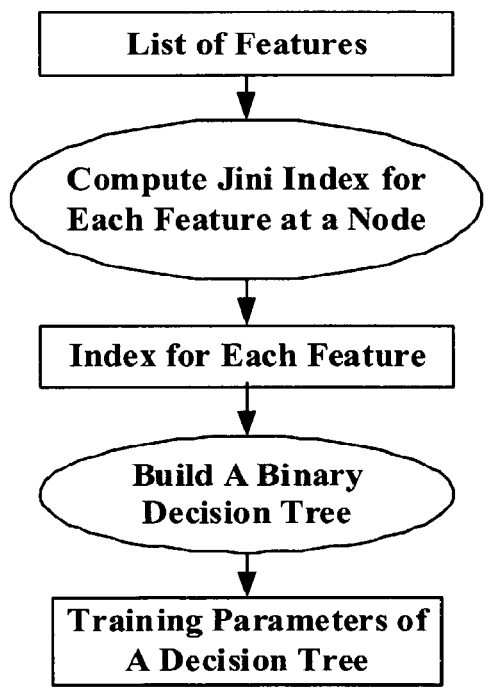
FIG. 29 illustrates an embodiment of a process of decision tree construction.

FIG. 29 illustrates an embodiment of a process of decision tree construction. In this process a jini index is computed for each feature at a node to find the best feature in the node. A threshold is automatically decided to have binary decision, which generates left and right child nodes. A binary decision tree is built. The binary decision tree classifier is one of most powerful classification tools available. It can approach to arbitrary class boundary. The training parameters obtained from the built decision tree are then used for online test.

Figure 30:
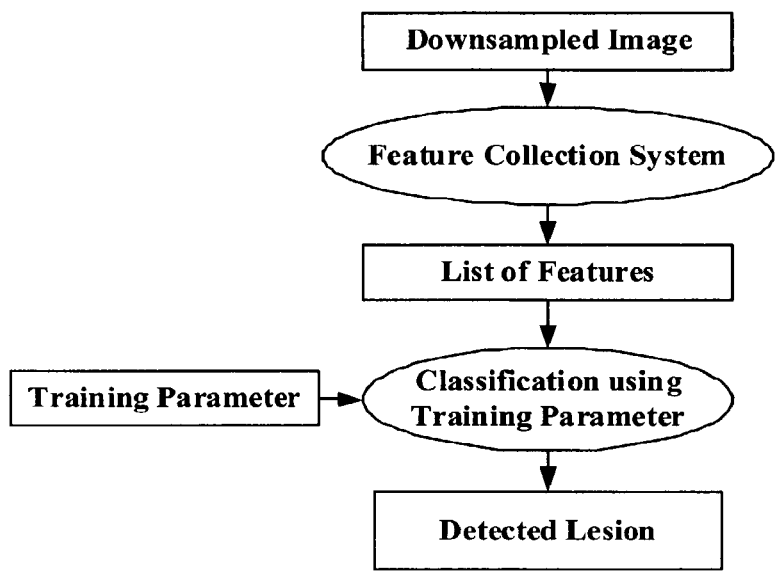
FIG. 30 depicts an embodiment of an online lesion detection system.

FIG. 30 depicts an embodiment of an online lesion detection system. The system uses the same feature collection system as shown in the training system. The training parameters are then applied to classify online testing mammograms. The detected lesion is used to guide the ultrasound imaging to obtain a fast and localized 3-D slices of breast in the lesion area.

In conclusion, embodiments of full-field digital mammography (FFDM) and ultrasound screening systems are disclosed in which ultrasound (US) image acquisition is driven by a software imaging method in a selected area. Isotropic volumes can be generated. Fast lesion detection X-ray modality can guide the generation of isotropic volume for US modality in the reduced breast area. Embodiments improve the specificity and sensitivity of the screening. Scanning with the second modality can be guided by the first modality. Embodiments include automatic ultrasound scanning along with the X-ray scanning system. Embodiments provide extensibility to new patient databases since the system training is performed offline and the training parameters are updated online. Segmentation and supervised detection facilitate lesion detection process. Adaptive localized thresholding enhances segmentation of faint lesions. Morphological processing enhances segmentation of lesion candidates are improved because morphological processing enables imaging of connected objects and removal of isolated small objects.

Some embodiments employ down-sampling based on multi-resolution, which reduces the processing area and improves the speed of the overall system. Edges are preserved with multi-resolution based down-sampling. The selection of thresholds is automatic and adaptive because threshold selection is based on histogram analysis in the localized windows. In some embodiments fast lesion detection is performed on an extracted region of interest (ROI) only. Thus, the background is processed as a breast area.

Various embodiments employ spline fitting to extract the breast-skin boundary. Features, such as texture and shape features are used to differentiate true lesions from false lesions, thereby reducing the number of false positive results. Embodiments employ wavelet based multi-resolution analysis to reduce the effects due to lesion and/or breast size variation. The collection of features can allow the expansion of database without change of the framework. The collection of features can be developed offline, with a subset of features being used for online detection. The expansion of feature database may change the subset of features.

Embodiments employ a classification system based on a decision tree. The decision tree can approach an arbitrary boundary to obtain a low misclassification rate. Embodiments of the fast lesion detection system can be used as a stand-alone computer-aided detection (CAD) system. The fast online lesion detection system can be available at the mammography screening. Some embodiments are module-based, thereby allowing each module to be individually developed and modified. Modules can be easily integrated into other systems or used as the stand-alone applications.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A method comprising:
acquiring a medical image of a patient using a first imaging modality;
computer-processing the image to identify a sub-region of the image that contains a suspected abnormality;
acquiring a medical image of the sub-region using a different imaging modality; and
displaying results related to said image of the sub-region acquired with the different imaging modality;
wherein one of the modalities is x-ray imaging and the other is ultrasound imaging.

2. The method of claim 1 in which the medical image acquired with the first imaging modality is a medical x-ray image of the patient.

3. The method of claim 1 in which the medical image acquired with the second imaging modality is a medical ultrasound image of the patient.

4. The method of claim 1 in which the medical image acquired with the first modality is a medical x-ray image and the medical image acquired with the second imaging modality is an ultrasound medical image.

5. The method of claim 1 in which the medical image acquired with the first imaging modality comprises plural 2D x-ray images of the patient.

6. The method of claim 5 in which the processing is configured to computer-process the plural 2D images to identify the sub-region that contains a suspected abnormality.

7. The method of claim 1 in which the processing is configured to segment the medical image acquired with the first modality into plural segments and to provide segmented imaging data.

8. The method of claim 7 in which the processing is configured to perform multi-resolution analysis in conjunction with providing the segmented imaging data so as to preserve selected features of the imaging data at high resolution but reduce an overall image quality.

9. The method of claim 8 in which the processor is configured to conduct morphological processing to process imaging data extending over more than one segment of the segmented imaging data.

10. The method of claim 1 in which the first imaging modality acquires an x-ray mammogram of the patient.

11. A system comprising:
- a first imaging structure acquiring a medical image of a patient using a first imaging modality;
- a processor configured to computer-process the image to identify a sub-region of the image that contains a suspected abnormality;
- a second imaging structure acquiring a medical image of the sub-region using a different imaging modality; and
- a display configured to display results related to said image of the sub-region acquired with the different imaging modality.
- wherein one of the modalities is x-ray imaging and the other is ultrasound imaging.

12. The system of claim 11 in which the first imaging structure comprises an x-ray imaging structure acquiring a medical x-ray image of the patient.

13. The system of claim 11 in which the second imaging structure comprises an ultrasound imaging structure acquiring a medical ultrasound image of the patient.

14. The system of claim 11 in which the first imaging structure is an x-ray imaging structure and the second imaging structure is an ultrasound imaging structure.

15. The system of claim 11 in which the first imaging structure is an x-ray imaging structure acquiring a medical image comprising plural 2D x-ray images of the patient.

16. The system of claim 15 in which the processor is configured to computer-process the plural 2D images to identify the sub-region that contains a suspected abnormality.

17. The system of claim 11 in which the processor is configured to segment the medical image acquired with the first modality into plural segments and to provide segmented imaging data.

18. The system of claim 17 in which the processor is configured to perform multi-resolution analysis in conjunction with providing the segmented imaging data so as to preserve selected features of the imaging data at high resolution but reduce an overall image quality.

19. The system of claim 17 in which the processor is configured to conduct morphological processing to process imaging data extending over more than one segment of the segmented imaging data.

20. The system of claim 11 in which the first imaging structure acquires an x-ray mammogram of the patient.

* * * * *